US008883154B2

(12) United States Patent
Goldblum et al.

(10) Patent No.: US 8,883,154 B2
(45) Date of Patent: Nov. 11, 2014

(54) ANTIBODY-MEDIATED MODULATION OF ALLERGY

(75) Inventors: Randall M. Goldblum, Dickinson, TX (US); Terumi Midoro-Horiuti, Galveston, TX (US); Bo Ning, Galveston, TX (US); Ruby Tiwari, Palmerston North (NZ)

(73) Assignee: The Board of Regents of the University of Texas Systems, Austin, TX (US)

( * ) Notice: Subject to any disclaimer, the term of this patent is extended or adjusted under 35 U.S.C. 154(b) by 248 days.

(21) Appl. No.: 12/653,443

(22) Filed: Dec. 14, 2009

(65) Prior Publication Data

US 2010/0104571 A1 Apr. 29, 2010

Related U.S. Application Data

(63) Continuation-in-part of application No. PCT/US2008/007453, filed on Jun. 13, 2008.

(60) Provisional application No. 60/934,518, filed on Jun. 14, 2007.

(51) Int. Cl.
*A61K 39/395* (2006.01)
*C07K 16/00* (2006.01)
*C07K 16/16* (2006.01)
*A61K 39/00* (2006.01)

(52) U.S. Cl.
CPC .......... *C07K 16/16* (2013.01); *A61K 2039/505* (2013.01); *C07K 2317/622* (2013.01)
USPC .................. 424/141.1; 424/158.1; 424/171.1; 514/1.1; 530/387.1; 530/388.1; 530/388.26

(58) Field of Classification Search
None
See application file for complete search history.

(56) References Cited

PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994. 491-495.*
Colman et al. 'Effects of amino acid sequence changes on antibody-antigen interactions.' Research in Immunology. 145(1):33-36, 1994.*
Abaza et al. 'Effects of amino acid substitutions outside an antigenic site on protein binding to monoclonal antibodies of predetermined specificity obtained by peptide immunization: demonstration with region 94-100 (antigenic site 3) of myoglobin. Journal of Protein Chemistry.' 11(5):433-444, 1992.*
Lederman et al. °A single amino acid substitution in a common African allele of the CD4 molecule ablates binding of the monoclonal antibody, OKT4. Molecular Immunology. 28:1171-1181, 1991.*
Midoro-Horiuti et al., Structural basis for epitope sharing between group I allergens of cedar pollen, Molecular Immunology, 2006, 43:509-18.
Sakaguchi et al., Epitope specificity of IgE antibodies to a major allergen (Cry j 1) of Japanese cedar pollen in sera of humans and monkeys with pollinosis, Immunology, 1997, 91:161-66.
Somen et al., Homology modeling and characterization of IgE binding epitopes of mountain cedar allergen Jun a 3, Biophysical Journal, 2000, 79:1601-09.
Varshney et al., Major mountain cedar allergen, Jun a 1, contains conformational as well as linear IgE epitopes, Molecular Immunology, 2007, 44:2781-85.

* cited by examiner

*Primary Examiner* — Nora Rooney

(57) ABSTRACT

The present invention is drawn to antibody-mediated modulation of allergy. In this regard, the present invention discloses a monoclonal antibody, antigen-binding fragment or mimic thereof directed against Group 1 pollen allergens or homologues thereof. Also disclosed herein is the mechanism by which the disclosed monoclonal antibody, antigen binding fragment or mimic thereof will improve immunotherapy of allergic reactions in an individual. It is contemplated that herein that such a monoclonal antibody, antigen binding fragment or mimic thereof may also be useful in treatment of several microbial infections.

6 Claims, 8 Drawing Sheets

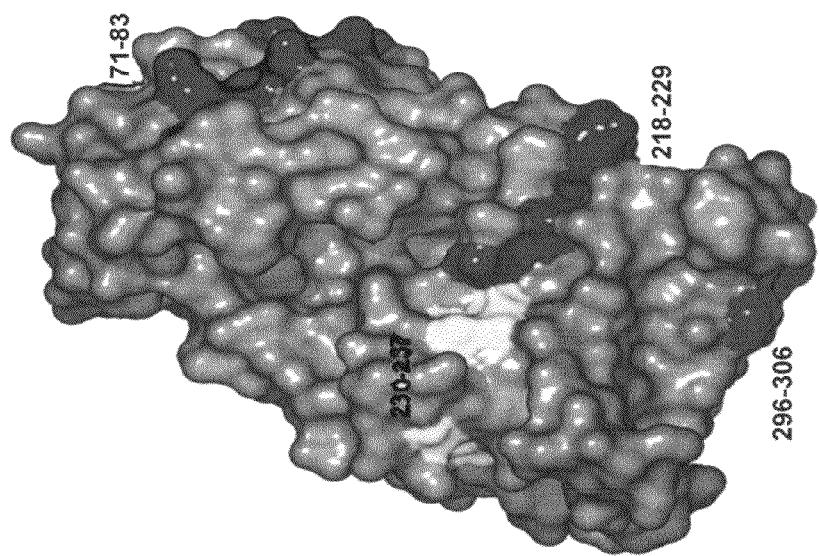

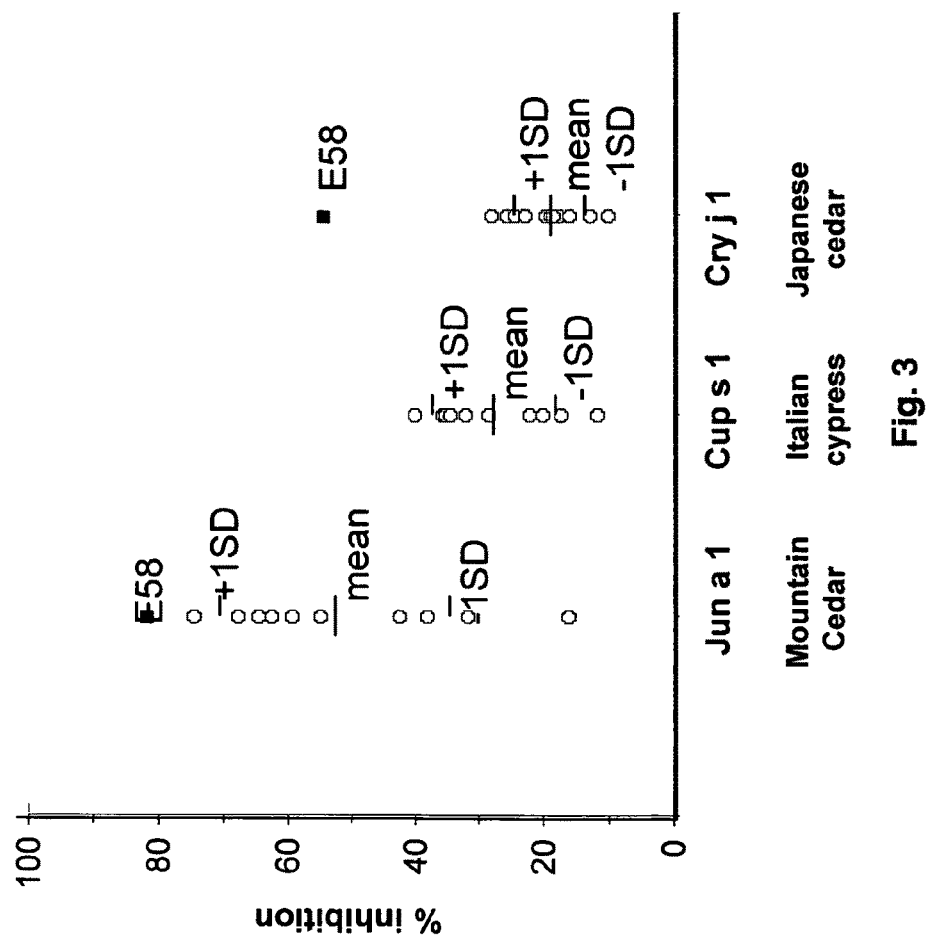

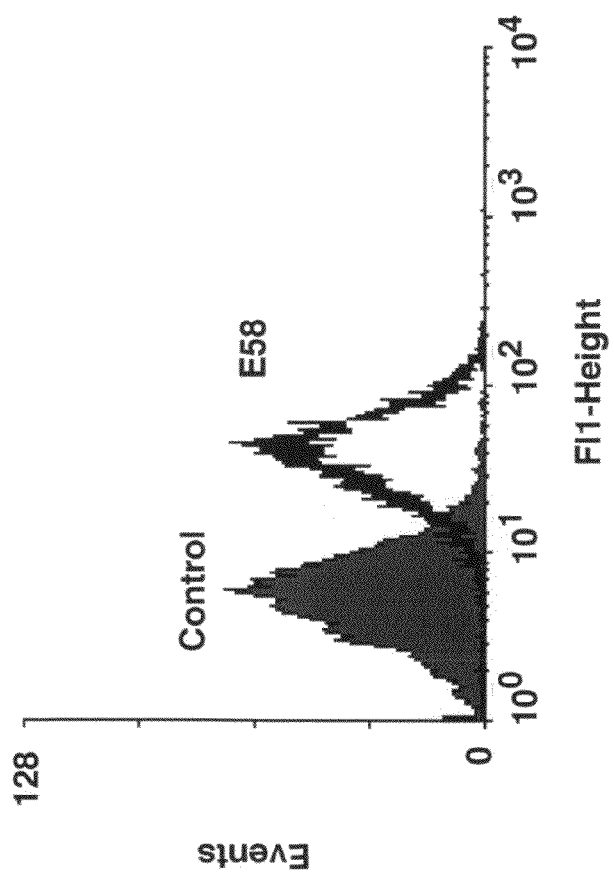

SEQUENCE LISTING

```
<160> NUMBER OF SEQ ID NOS: 13

<210> SEQ ID NO 1
<211> LENGTH: 367
<212> TYPE: PRT
<213> ORGANISM: artificial sequence
<220> FEATURE:
<223> OTHER INFORMATION: Jun a 1 allergen protein sequence

<400> SEQUENCE: 1

Met Ala Ser Pro Cys Leu Ile Ala Val Leu Val Phe Leu Cys Ala
1               5                   10                  15

Ile Val Ser Cys Tyr Ser Asp Asn Pro Ile Asp Ser Cys Trp Arg
                20                  25                  30

Gly Asp Ser Asn Trp Asp Gln Asn Arg Met Lys Leu Ala Asp Cys
                35                  40                  45

Ala Val Gly Phe Gly Ser Ser Thr Met Gly Gly Lys Gly Gly Asp
                50                  55                  60

Phe Tyr Thr Val Thr Ser Thr Asp Asp Asn Pro Val Asn Pro Thr
                65                  70                  75

Pro Gly Thr Leu Arg Tyr Gly Ala Thr Arg Glu Lys Ala Leu Trp
                80                  85                  90

Ile Ile Phe Ser Gln Asn Met Asn Ile Lys Leu Lys Met Pro Leu
                95                  100                 105

Tyr Val Ala Gly His Lys Thr Ile Asp Gly Arg Gly Ala Asp Val
                110                 115                 120

His Leu Gly Asn Gly Gly Pro Cys Leu Phe Met Arg Lys Val Ser
                125                 130                 135
```

-continued

```
His Val Ile Leu His Ser Leu His Ile His Gly Cys Asn Thr Ser
                140                 145                 150

Val Leu Gly Asp Val Leu Val Ser Glu Ser Ile Gly Val Glu Pro
                155                 160                 165

Val His Ala Gln Asp Gly Asp Ala Ile Thr Met Arg Asn Val Thr
                170                 175                 180

Asn Ala Trp Ile Asp His Asn Ser Leu Ser Asp Cys Ser Asp Gly
                185                 190                 195

Leu Ile Asp Val Thr Leu Gly Ser Thr Gly Ile Thr Ile Ser Asn
                200                 205                 210

Asn His Phe Phe Asn His His Lys Val Met Leu Leu Gly His Asp
                215                 220                 225

Asp Thr Tyr Asp Asp Asp Lys Ser Met Lys Val Thr Val Ala Phe
                230                 235                 240

Asn Gln Phe Gly Pro Asn Ala Gly Gln Arg Met Pro Arg Ala Arg
                245                 250                 255

Tyr Gly Leu Val His Val Ala Asn Asn Asn Tyr Asp Pro Trp Asn
                260                 265                 270

Ile Tyr Ala Ile Gly Gly Ser Ser Asn Pro Thr Ile Leu Ser Glu
                275                 280                 285

Gly Asn Ser Phe Thr Ala Pro Ser Glu Ser Tyr Lys Lys Glu Val
                290                 295                 300

Thr Lys Arg Ile Gly Cys Glu Ser Pro Ser Ala Cys Ala Asn Trp
                305                 310                 315

Val Trp Arg Ser Thr Arg Asp Ala Phe Ile Asn Gly Ala Tyr Phe
                320                 325                 330

Val Ser Ser Gly Lys Thr Glu Glu Thr Asn Ile Tyr Asn Ser Asn
                335                 340                 345

Glu Ala Phe Lys Val Glu Asn Gly Asn Ala Ala Pro Gln Leu Thr
                350                 355                 360

Lys Asn Ala Gly Val Val Thr
                365
```

<210> SEQ ID NO 2
<211> LENGTH: 1104
<212> TYPE: DNA
<213> ORGANISM: artificial sequence
<220> FEATURE:
<223> OTHER INFORMATION: nucleotide sequence of Jun a 1 allergen

<400> SEQUENCE: 2

```
atggcttccc catgcttaat agcagtcctt gttttccttt gtgcaattgt          50
atcttgttac tctgataatc ccatcgacag ctgctggaga ggagattcga         100
actgggatca aaacagaatg aagctcgcag actgtgctgt gggatttgga         150
agctccacca tgggaggcaa aggaggagat ttttacaccg tcacaagcac         200
agatgataat cctgtgaatc ctacaccagg aactttgcgc tatggagcaa         250
caagagaaaa agcactttgg atcattttct ctcagaatat gaatataaag         300
ctcaagatgc ctttgtatgt tgctggacat aagactattg acggcagggg         350
agcagatgtt catcttggca acggcggtcc ctgtctgttt atgaggaaag         400
tgagccatgt tattctccat agtttgcata tacacggttg taatacgagt         450
gttttggggg atgttttggt aagtgagtct attggggtgg agcctgttca         500
```

```
tgctcaggat ggggacgcca ttactatgcg caatgttaca aatgcttgga      550
ttgatcataa ttctctctcc gattgttctg atggtcttat cgatgttacg      600
cttggctcca ctggaattac tatctccaac aatcacttct tcaaccatca      650
taaagtgatg ttgttaggac atgatgatac atatgacgat gacaaatcta      700
tgaaagtgac agtggcgttc aatcaatttg gacctaatgc tgggcaaaga      750
atgccaaggg cacgatatgg acttgtacat gtcgcaaaca ataattatga      800
tccatggaat atatatgcta ttggtgggag ttcaaatcca accattctaa      850
gtgaagggaa tagtttcact gccccaagtg agagctacaa gaaggaagta      900
acaaagcgta tagggtgtga atcaccatca gcttgtgcga actgggtgtg      950
gagatctaca cgagatgctt ttattaatgg agcttatttt gtatcatcgg     1000
ggaaaactga agagaccaat atatacaata gtaatgaagc tttcaaagtt     1050
gagaatggga atgcagctcc tcaattaacc aaaaatgctg agttgtaac      1100
ctaa                                                       1104
```

<210> SEQ ID NO 3
<211> LENGTH: 225
<212> TYPE: PRT
<213> ORGANISM: artificial sequence
<220> FEATURE:
<223> OTHER INFORMATION: Jun a 3 allergen protein sequence

<400> SEQUENCE: 3

```
Met Ala Arg Val Ser Glu Leu Ala Phe Leu Leu Ala Ala Thr Leu
1               5                   10                  15

Ala Ile Ser Leu His Met Gln Glu Ala Gly Val Val Lys Phe Asp
                20                  25                  30

Ile Lys Asn Gln Cys Gly Tyr Thr Val Trp Ala Ala Gly Leu Pro
                35                  40                  45

Gly Gly Gly Lys Arg Leu Asp Gln Gly Gln Thr Trp Thr Val Asn
                50                  55                  60

Leu Ala Ala Gly Thr Ala Ser Ala Arg Phe Trp Gly Arg Thr Gly
                65                  70                  75

Cys Thr Phe Asp Ala Ser Gly Leu Gly Ser Cys Gln Thr Gly Asp
                80                  85                  90

Cys Gly Gly Gln Leu Ser Cys Thr Val Ser Gly Ala Val Pro Ala
                95                  100                 105

Thr Leu Ala Glu Tyr Thr Gln Ser Asp Gln Asp Tyr Tyr Asp Val
                110                 115                 120

Ser Leu Val Asp Gly Phe Asn Ile Pro Leu Ala Ile Asn Pro Thr
                125                 130                 135

Asn Ala Gln Cys Thr Ala Pro Ala Cys Lys Ala Asp Ile Asn Ala
                140                 145                 150

Val Cys Pro Ser Glu Leu Lys Val Asp Gly Gly Cys Asn Ser Ala
                155                 160                 165

Cys Asn Val Phe Lys Thr Asp Gln Tyr Cys Cys Arg Asn Ala Tyr
                170                 175                 180

Val Asp Asn Cys Pro Ala Thr Asn Tyr Ser Lys Ile Phe Lys Asn
                185                 190                 195

Gly Cys Pro Gln Ala Tyr Ser Tyr Ala Lys Asp Asp Thr Ala Thr
                200                 205                 210
```

Phe Ala Cys Ala Ser Gly Thr Asp Tyr Ser Ile Val Phe Cys Pro
                215                 220                 225

<210> SEQ ID NO 4
<211> LENGTH: 678
<212> TYPE: DNA
<213> ORGANISM: artificial sequence
<220> FEATURE:
<223> OTHER INFORMATION: nucleotide sequence encoding Jun a 3 allergen
      protein

<400> SEQUENCE: 4

| | | |
|---|---|---|
| atggcccgag tatcagagct tgcgtttctt cttgcggcca cattggccat | 50 |
| ctctttacac atgcaagagg cgggagtagt gaagtttgat ataaagaacc | 100 |
| agtgcgggta cacagtctgg gcagcggggt tgcccggagg agggaagcgg | 150 |
| cttgaccagg ggcagacatg gacggttaat ttggcggcgg gcacagcgtc | 200 |
| ggcaaggttc tggggacgaa cgggctgcac tttcgatgcg agcgggaaag | 250 |
| gaagctgcca gaccggtgac tgcggcgggc aactgagctg cacagtctcc | 300 |
| ggagcagttc ccgcgacgct ggcagagtac acgcagagcg accaggacta | 350 |
| ctacgacgta tccctcgtcg atggcttcaa cattcctctt gccatcaacc | 400 |
| caacgaatgc acagtgcacc gctcctgcct gcaaggctga cattaatgca | 450 |
| gtgtgccctt ccgagttgaa ggttgatggc ggatgcaata cgcctgcaa | 500 |
| tgtcttcaaa actgatcagt attgctgcag aaatgcgtat gttgataact | 550 |
| gccctgccac gaattactcc aagatattca gaaccagtg ccctcaggct | 600 |
| tacagctatg ccaaggatga cacggccact ttcgcttgcg cctctggtac | 650 |
| cgactacagt attgtattct gcccctag | 678 |

<210> SEQ ID NO 5
<211> LENGTH: 13
<212> TYPE: PRT
<213> ORGANISM: artificial sequence
<220> FEATURE:
<223> OTHER INFORMATION: Jun a 1 allergen epitope sequence

<400> SEQUENCE: 5

Ile Phe Ser Gln Asn Met Asn Ile Lys Leu Lys Met Pro
1               5                   10

<210> SEQ ID NO 6
<211> LENGTH: 12
<212> TYPE: PRT
<213> ORGANISM: artificial sequence
<220> FEATURE:
<223> OTHER INFORMATION: Jun a 1 allergen epitope sequence

<400> SEQUENCE: 6

Ala Phe Asn Gln Phe Gly Pro Asn Ala Gly Gln Arg
1               5                   10

<210> SEQ ID NO 7
<211> LENGTH: 8
<212> TYPE: PRT
<213> ORGANISM: artificial sequence
<220> FEATURE:
<223> OTHER INFORMATION: Jun a 1 allergen epitope sequence

<400> SEQUENCE: 7

Met Pro Arg Ala Arg Tyr Gly Leu
1               5

```
<210> SEQ ID NO 8
<211> LENGTH: 11
<212> TYPE: PRT
<213> ORGANISM: artificial sequence
<220> FEATURE:
<223> OTHER INFORMATION: Jun a 1 allergen epitope sequence

<400> SEQUENCE: 8

Trp Arg Ser Thr Arg Asp Ala Phe Ile Asn Gly
1               5                   10

<210> SEQ ID NO 9
<211> LENGTH: 13
<212> TYPE: PRT
<213> ORGANISM: artificial sequence
<220> FEATURE:
<223> OTHER INFORMATION: Jun a 3 allergen epitope sequence

<400> SEQUENCE: 9

Ala Ala Gly Thr Ala Ser Ala Arg Phe Trp Gly Arg Thr
1               5                   10

<210> SEQ ID NO 10
<211> LENGTH: 13
<212> TYPE: PRT
<213> ORGANISM: artificial sequence
<220> FEATURE:
<223> OTHER INFORMATION: Jun a 3 allergen epitope sequence

<400> SEQUENCE: 10

Thr Phe Asp Ala Ser Gly Lys Gly Ser Cys Gln Thr Gly
1               5                   10

<210> SEQ ID NO 11
<211> LENGTH: 12
<212> TYPE: PRT
<213> ORGANISM: artificial sequence
<220> FEATURE:
<223> OTHER INFORMATION: Jun a 3 allergen epitope sequence

<400> SEQUENCE: 11

Ala Asp Ile Asn Ala Val Cys Pro Ser Glu Leu Lys
1               5                   10

<210> SEQ ID NO 12
<211> LENGTH: 14
<212> TYPE: PRT
<213> ORGANISM: artificial sequence
<220> FEATURE:
<223> OTHER INFORMATION: Jun a 3 allergen epitope sequence

<400> SEQUENCE: 12

Val Asp Gly Gly Cys Asn Ser Ala Cys Asn Val Phe Lys Thr
1               5                   10

<210> SEQ ID NO 13
<211> LENGTH: 14
<212> TYPE: PRT
<213> ORGANISM: artificial sequence
<220> FEATURE:
<223> OTHER INFORMATION: Jun a 3 allergen epitope sequence

<400> SEQUENCE: 13

Asn Ala Tyr Val Asp Asn Cys Pro Ala Thr Asn Tyr Ser Lys
1               5                   10
```

ANTIBODY-MEDIATED MODULATION OF ALLERGY

CROSS-REFERENCE TO RELATED APPLICATIONS

Figure 2A:
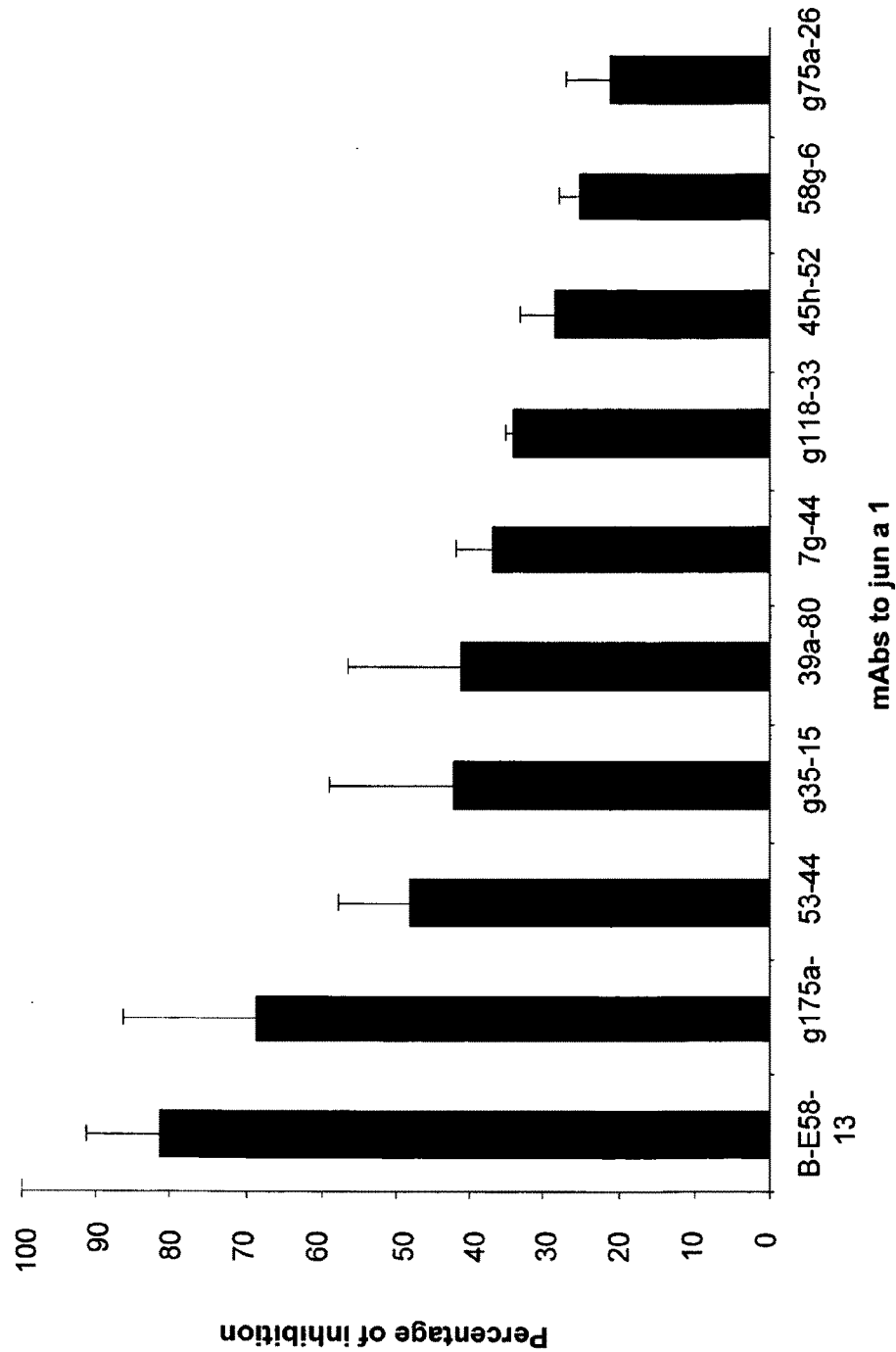

This continuation-in-part applications claims benefit of priority under 35 U.S.C. §120 of international application PCT/US2008/007453, filed Jun. 13, 2008, which claims benefit of priority under 35 U.S.C. 119(e) of provisional U.S. Ser. No. 60/934,518, filed Jun. 14, 2007, the entirety of both of which are hereby incorporated by reference.

This invention was made with government support under 5R01A1052428-03 and A1055792 awarded by the National Institute of Allergy and Infectious Diseases (NIAID). The government has certain rights in the invention.

BACKGROUND OF THE INVENTION

1. Field of the Invention

The present invention relates to the fields of immunology and allergology. More specifically, the present invention discloses monoclonal antibodies to allergen and their use in prevention of allergic symptoms.

2. Description of the Related Art

Hypersensitivity to aeroallergens is a major cause of allergic diseases, e.g. bronchial asthma, allergic rhinitis and allergic conjunctivitis), that affect up to 30% of some populations (1-2). In the United States, about 39 million persons were estimated to have experienced allergic rhinitis (3). Symptoms of rhinitis and asthma due to aeroallergens cause extensive morbidity, lost productivity and increased health care cost (4). Allergic rhinitis accounts for more than 10 million office visits for medical care and millions of days of restricted activity each year in the U.S. The clinical efficacy of the current pharmaco- and immunotherapy for plant-induced allergic diseases is limited. The total monetary cost of the condition is estimated to be $6 billion.

The pollen of various plants, including trees, grasses and weeds are responsible for many of the allergic reactions that occur outdoor during specific seasons. Cedar hypersensitivity is one of the most common causes of seasonal allergic disease in numerous regions around the world. Japanese cedar (*Cryptomeria japonica*, Taxodiaceae) is the major cause of pollinosis in Japan (5), while mountain cedar (*Juniperus ashei*, Cupressaceae) pollen caused severe seasonal allergic rhinitis in North America (particularly, Arkansas, Oklahoma, central Texas, and Northern Mexico) (6-7) and Arizona and italian cypresses (*Cupressus arizonica* and simperverins, Cupressaceae) causes pollinosis in the Mediterranean region (France, Italy and Israel) (8-9).

Additionally, individuals with hypersensitivity to one member of the Cupressaceae and Taxodiaceae families have been shown to have extensive cross-reactivity to other members of the Cupressaceae family by acute hypersensitivity skin testing (7). This could be due to similarities in the structures of the proteins in the pollen from different trees.

Altered regulation of IgE antibody formation is the hallmark of the allergic diathesis. Normal individuals exposed to inhaled aeroallergens produce small amounts of IgG1 and IgG4 antibodies in association with proliferation of T helper 1 (Th1) cells. Patients with an allergic diathesis tend to have exaggerated responses of their T helper 2 (Th2) cells and produce large amount of allergen-specific IgE (10). This "allergic" response is most likely due at least in part, to genetic propensities to overexpress families of cytokine genes, e.g. IL-4, IL-5 and IL-13. However, the process of allergic sensitization also depends on the amount, duration and group of allergen exposures. In general, small concentrations of allergenic protein delivered to the mucosal surface are most effective in this respect (11). Allergic or atopic individuals typically have elevated serum IgE concentrations and IgE antibodies to multiple epitopes of a number of environmental allergens. When the IgE near the mucosal surface reaches a high enough concentration and is directed against an adequate number of epitopes on the allergen, an allergic reaction can ensue.

The immune complexes that induce basophil/mast cell degranulation consist of at least five molecules on the outer surface of the cell: at least two IgE molecules usually of different antibody specificity; each bound to an α-chain of an FcER1 and an allergen with at least two epitopes, recognized by IgE molecules. While the crystal structure of complexes containing the interacting portions of the FcER1 and IgE molecules have been resolved, much less is known about the structural requirements of specific allergens to participate in the formation of activating complexes. Further, identifying these epitopes is a critical step in understanding the structural requirements for allergens to complete the pentameric complex that signals the basophil or mast cell to activate and release its mediators and other bioactive molecules.

Since avoidance of allergens is usually not a practical approach for managing hypersensitivity to outdoor plants, pharmacological therapy with anti-histamines, leukotriene antagonists and topical steroids are the mainstays of current therapy. However, these modalities have their limitations and adverse effects. Preventive or therapeutic immunization (immunotherapy) holds the greatest promise of preventing and treating acute hypersensitivity diseases. However, current allergy immunotherapy requires frequent injection of increasing amounts of crude extracts of the offending allergen and takes months to years to become effective. Immunization-induced changes in the inflammatory cascade are thought to be responsible for diminishing or abolishing the allergic reactions to natural exposure. The production of specific IgG antibodies may interfere with the delivery of the allergens to mast cells or the development of IgE-containing, activating complexes on the cell surface. Additionally, decreased numbers and activity of several inflammatory cell groups have been seen after allergen immunotherapy. Most of these changes are thought to be secondary to shifts in the T helper cells from Th2 to Th1 group (10μ, 12). However, there is also evidence for T cell unresponsiveness or anergy after immunotherapy (13). Furthermore, the long term protection of this form of immunization is similar to those achieved with anti-microbial vaccines in that the effect can last for a number of years after stopping or reducing the frequency of injections (14).

Despite the fact that immunotherapy for allergic disease has been practiced for almost 100 years, it has yet to achieve its full potential. This is largely because injecting increasing doses of crude extracts of sensitizing agents carries a risk for generalized and potentially fatal anaphylaxis. To avoid anaphlaxis, the allergen injections must be started at very low doses and increased gradually through a long series of injections. Attempts to reduce the anaphylaxis risk by chemically modifying the allergens with agents like formaldehyde, which reduce the binding of patient's IgE to the injected allergens have failed because they can also reduce the immunogenicity of the allergens. Another approach is to clone the major allergens and disrupt the structure of one or more of their IgE epitopes by site-directed mutagenesis. However, a drawback of this approach is the high cost of testing the safety of each of the mutagenized allergens in human subjects.

An alternate approach to obtain modified allergens would be to identify naturally occurring homologues of the sensitizing allergens within the same or similar plants. In fact, some allergens are shown as expressed as a family of closely related proteins or isoforms within the same plant and species of plants (15-16 Ferreira et al., 1996: Ferreira et al., 1997).

Previous studies identified two major allergens in the pollen of the mountain cedar tree. The first of these was named Jun a 1 (17 Midoro-Horiuti et al., 1999) because of its similarity to Cry j 1, an important allergen of Japanese cedar. Two cypress trees from southern Europe were later found to express highly allergenic homologues of Jun a1. Jun a1 dominates the allergic response to mountain cedar pollen and is therefore a therapeutic target in cedar pollinosis. Additionally, four linear IgE epitopes were mapped on the surface of Jun a1 (18 Czerwinski et al., 2005).

Despite these advances, the prior art is deficient in the identification of effective therapeutic agents that can prevent allergens from inducing allergic reactions. The present invention fulfills this long-standing need and desire in the art.

SUMMARY OF THE INVENTION

In one embodiment of the present invention, there is provided a monoclonal antibody or an antigen-binding fragment thereof directed against a Group I pollen allergen. This antibody or antigen-binding fragment thereof alters the structure of the allergen in such a way that it reduces or prevents its capacity to interact with previously formed, IgE antibody to the allergen. In certain aspects the monoclonal antibody is the E58 monoclonal antibody. *E. coli* strain E-58 ScAb clone D6 comprising a plasmid encoding the amino acid sequence of single chain antibody E58 has been deposited on May 1, 2013 with the Agricultural Research Culture Collections, International Depository Authority, 1815 N. University Street, Peoria, Ill., USA (NRRL) in compliance with the Budapest treaty on the international recognition of the deposit of microorganisms for the purpose of patent procedures as NRRL deposit number B-50843.

In a related embodiment of the present invention, there is provided an immunologic composition. Such an immunologic composition comprises the monoclonal antibody or antigen-binding fragment thereof described supra and a pharmaceutically acceptable carrier.

In yet another related embodiment of the present invention, there is provided a method of preventing development of an allergic reaction to a pollen in an individual. Such a method comprises the step of administering therapeutically effective amounts of the immunologic composition described supra to the individual.

In another related embodiment of the present invention, there is provided an immunologic composition. Such an immunologic composition comprises the monoclonal antibody or antigen binding fragment thereof described supra, crude extract of pollen and a pharmaceutically acceptable carrier.

In a further related embodiment of the present invention, there is provided a method of improving pollen allergy immunotherapy in an individual. Such a method comprises the step of administering therapeutically effective amounts of the immunologic composition described supra to the individual.

In another embodiment of the present invention, there is provided a monoclonal antibody or an antigen-binding fragment thereof directed against a homologue or a fragment thereof that is at least 90% identical to the amino acid sequence of the Group 1 pollen allergens or a fragment thereof. Such a monoclonal antibody or antigen-binding fragment thereof alters structure of the homologue or the fragment thereof, inhibits the binding of an IgE antibody to the homologue or the fragment thereof or both.

In another related embodiment of the present invention, there is provided an immunologic composition. Such a composition comprises the monoclonal antibody or antigen-binding fragment thereof directed against a homologue or a fragment thereof that is at least 90% identical to the amino acid sequence of the Group 1 pollen allergens or fragment thereof and a pharmaceutically acceptable carrier.

In yet another related embodiment of the present invention, there is provided a method of preventing development of an allergic reaction to a pollen in an individual. This method comprises the step of administering therapeutically effective amounts of the immunologic composition as described supra to the individual.

In a further related embodiment of the present invention, there is provided an immunologic composition. Such a composition comprises the monoclonal antibody or the antigen-binding fragment thereof directed against a homologue or a fragment thereof that is at least 90% identical to the amino acid sequence of the Group 1 pollen allergens or fragment thereof, crude extracts of Group 1 pollen allergens and a pharmaceutically acceptable carrier.

In yet another related embodiment of the present invention, there is provided a method of improving pollen allergy immunotherapy in an individual. Such a method comprises the step of administering therapeutically effective amounts of the above-mentioned immunologic composition to the individual.

In another embodiment of the present invention, there is provided a monoclonal antibody or an antigen-binding fragment thereof directed against a homologue or a fragment thereof that is at least 80% identical to the amino acid sequence of the Group 1 pollen allergens or a fragment thereof. Such a monoclonal antibody or antigen binding fragment thereof alters structure of the homologue or the fragment thereof, inhibits the binding of an IgE antibody to the homologue or the fragment thereof or both.

In another related embodiment of the present invention, there is provided an immunologic composition, comprising the monoclonal antibody or the antigen binding-fragment thereof directed against a homologue or a fragment thereof that is at least 80% identical to the amino acid sequence of the Group 1 pollen allergens or a fragment thereof and a pharmaceutically acceptable carrier.

In yet another related embodiment of the present invention, there is provided a method of preventing development of an allergic reaction to pollen in an individual. Such a method comprises the step of administering therapeutically effective amounts of the above-mentioned immunologic composition to the individual.

In still yet another embodiment of the present invention, there is provided an immunologic composition. Such a composition comprises the monoclonal antibody or the antigen-binding fragment thereof described supra, crude extracts of Group 1 pollen allergens and a pharmaceutically acceptable carrier.

In another related embodiment of the present invention, there is provided a method of providing immunoprotection against Group 1 pollen allergens in an individual. Such a method comprises the step of administering therapeutically effective amounts of the above-mentioned immunologic composition to the individual.

BRIEF DESCRIPTION OF THE DRAWINGS

FIG. 1 shows crystal structure of Jun a1 showing locations of IgE epitopes. Epitope 1 (amino acid 71-83), epitope 2

(amino acid 218-229), epitope 3 (amino acid 230-237) and epitope 4 (amino acid 296-306). Only the backbone of the protein and three disulphide bonds are shown.

Figure 2B:
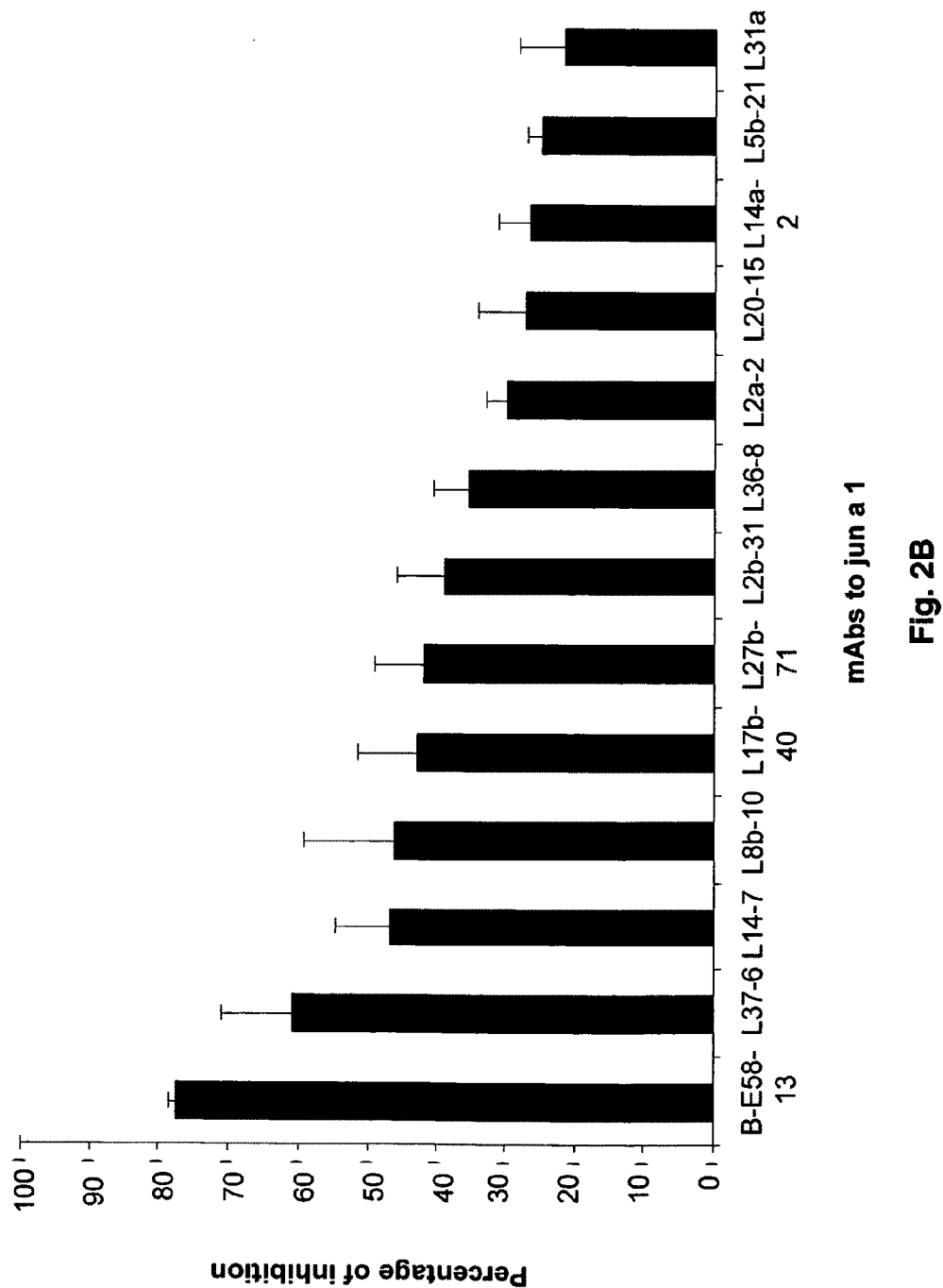

FIGS. 2A-2B show the degree to which monoclonal antibody E58 (an IgE class of mouse antibody) inhibits the binding of 21 other (IgG class) anti-Jun a1 monoclonal antibodies. The homologous inhibition (E58 inhibiting itself) is shown in each panel for comparison.

FIG. 3 shows inhibition of human serum IgE binding to allergen by mAb E58. Each circle represents an individual patient. Closed squares indicate the homologous inhibition of E58 binding.

FIG. 4 shows flow cytometric analysis of E. coli cells expressing an scAb form of E58, labeled with a Jun a1-BODIPY fluorescent conjugate.

Figure 5:
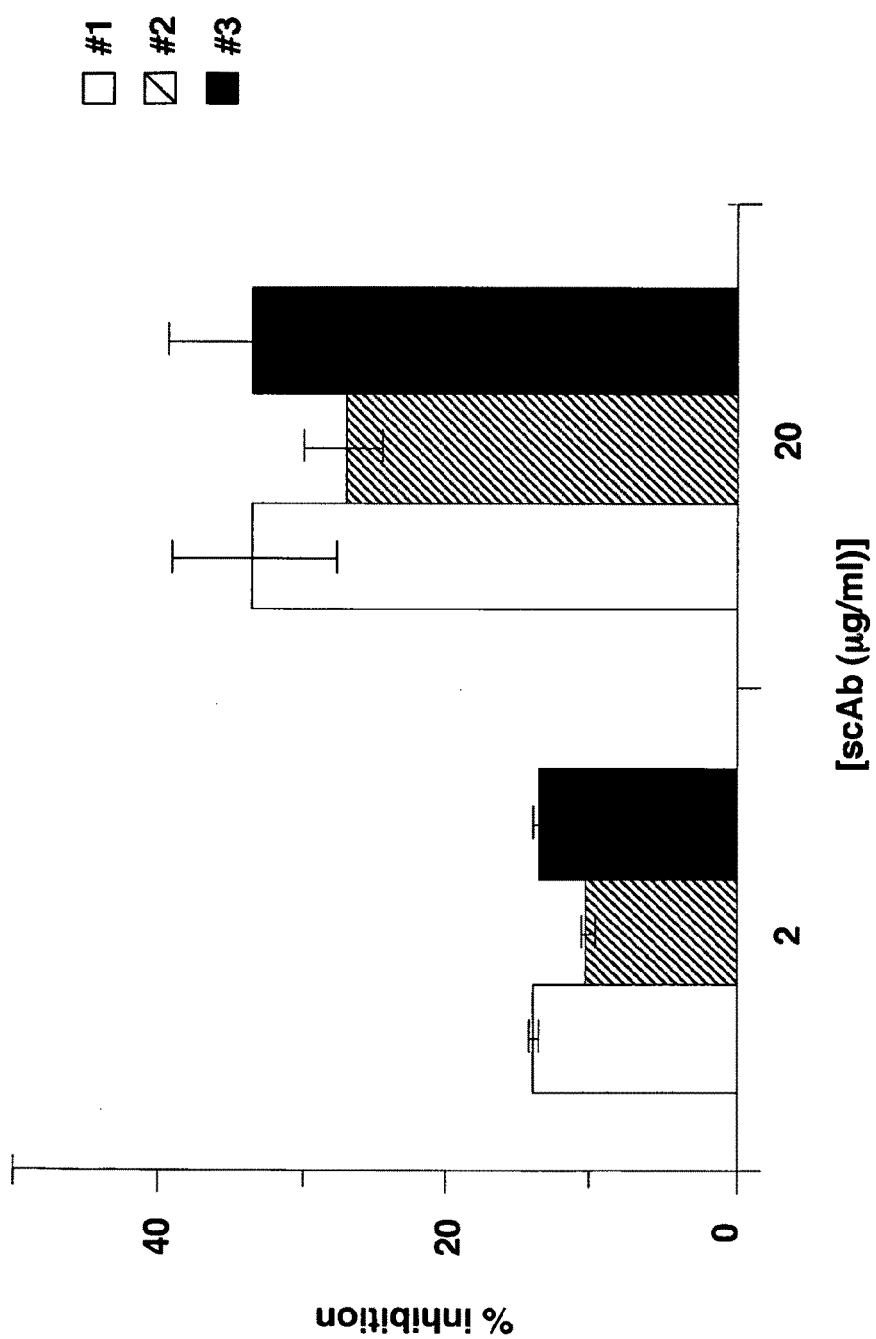

FIG. 5 shows recombinant E58-mediated inhibition of mast cell degranulation (β-hexosaminidase release). Numbers indicate an individual patient's serum used to sensitize the mast cells. Mean (±1 SE).

Figure 6:
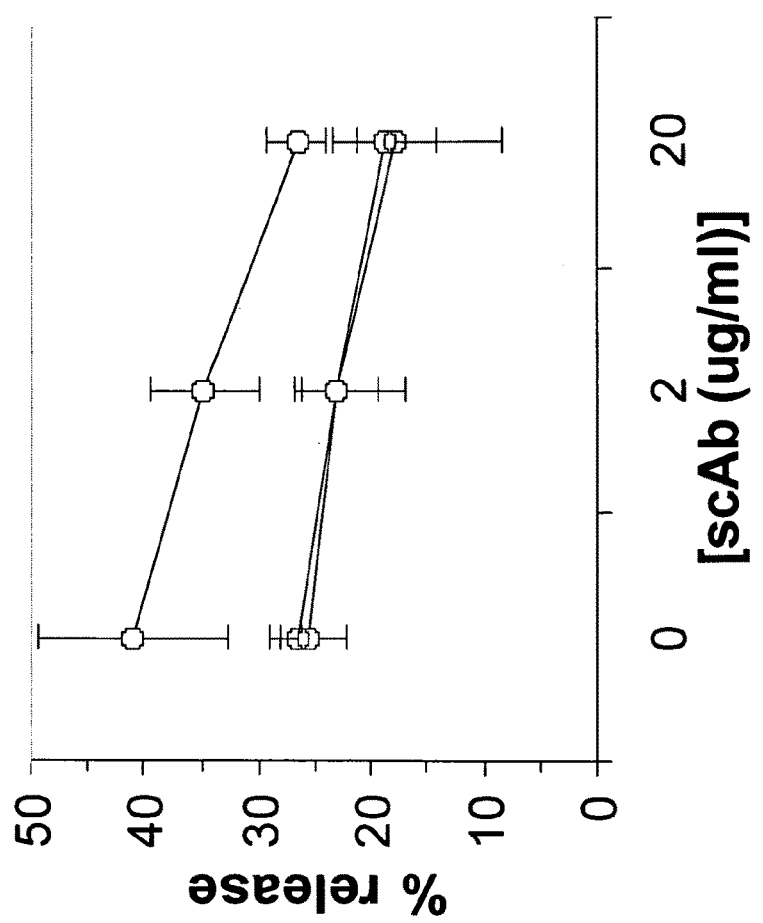

FIG. 6 shows that β-hexosaminidase release from mast cell was inhibited by recombinant E58. Each line represents mast cells sensitized with serum from an individual patient and stimulated with Jun a 1 alone (0 scAb) or Jun a 1 preincubated with E58. Mean (±1 SE).

Figure 7:
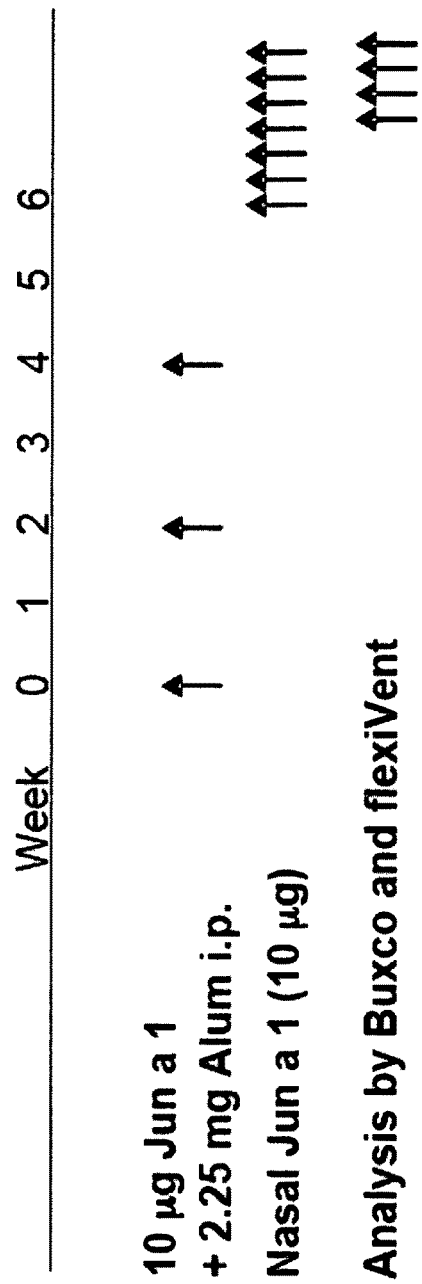

FIG. 7 shows results from a mouse model of allergic rhinitis. Respiratory frequency (Rf) was monitored (Buxco and flexiVent) over a period of 60 min after the nasal challenge with OVA or PBS. Results are from a single experiment with 2-4 OVA-sensitized mice in each group. *p<0.05 between PBS control and OVA sensitized groups.

DETAILED DESCRIPTION OF THE INVENTION

Although immunotherapy is an effective method to prevent or treat allergic diseases, it has not achieved its full potential for several reasons. First, injection of increased doses of the crude extracts of sensitizing agents carries a risk for generalized and potentially fatal anaphylaxis. Second, chemical modifications of the allergens with agents like formaldehyde reduce the immunogenicity of the allergens. Third, genetic modification of allergens is expensive with regards to testing the safety of each of the allergens that were mutagenized by disrupting the structure of one or more of their IgE epitopes by site-directed mutagenesis.

These drawbacks can be overcome by identifying naturally occurring homologues of the sensitizing allergens within the same or similar plants. In this regard, a previous study performed phylogenetic screening of naturally occurring homologues of the major pollen allergens of cedar trees and identified two major allergens. One of these allergens named Jun a1 and the nucleotide sequence (SEQ ID NO:2) encoding Jun a1 protein (SEQ ID NO:1) appear in the GenBank sequence data base under the Accession numbers AF106662 and AF106663. Jun a1 has a molecular weight and N-terminal amino acid sequence that is similar to that of the major allergen Cha o1, from Japanese cypress and Cry j 1, from Japanese cedar. IgE from the cedar hypersensitive patients bound to the isolated glycoprotein.

Another major protein peak from the reverse phase HPLC used to isolate allergens contained a protein with an apparent molecular weight of 30 KDa. This protein has the sequence of SEQ ID NO: 3. Since its N-terminal end had no homology to any of the other reported allergen, it was named Jun a 3. The nucleotide sequence encoding this protein has the sequence of SEQ ID NO:4 and is deposited in GenBank under accession number AF121776. Nucleotide sequences of Jun a 1 and Jun a 3 are shown in Table 1. Proteolytic and synthetic peptides derived from Jun a 1 and Jun a 3 were used to identify epitopes within Jun a 1 and Jun a 3 proteins. The sequences of Jun 3 a protein and of these epitopes are shown in Table 2. Jun 3 a epitopes are underlined in the Jun 3 a protein sequence.

TABLE 1

| Nucleotide sequences of Jun a 1 and Jun a 3 | | |
|---|---|---|
| | Accession No. | Nucleotide sequence |
| Jun a 1 | AF106662/ AF106663 SEQ ID NO: 2 | atggcttccc catgcttaat agcagtcctt gttttccttt gtgcaattgt atcttgttac tctgataatc ccatcgacag ctgctggaga ggagattcga actgggatca aaacagaatg aagctcgcag actgtgctgt gggatttgga agctccacca tgggaggcaa aggaggagat ttttacaccg tcacaagcac agatgataat cctgtgaatc ctacaccagg aactttgcgc tatggagcaa caagagaaaa agcactttgg atcattttct ctcagaatat gaatataaag ctcaagatgc ctttgtatgt tgctggacat aagactattg acggcagggg agcagatgtt catcttggca acggcggtcc ctgtctgttt atgaggaaag tgagccatgt tattctccat agtttgcata tacacggttg taatacgagt gttttggggg atgttttggt aagtgagtct attggggtgg agcctgttca tgctcaggat ggggacgcca ttactatgcg caatgttaca aatgcttgga ttgatcataa ttctctctcc gattgttctg atggtcttat cgatgttacg cttggctcca ctggaattac tatctccaac aatcacttct tcaaccatca taaagtgatg ttgttaggac atgatgatac atatgacgat gacaaatcta tgaaagtgac agtggcgttc aatcaatttg gacctaatgc tgggcaaaga atgccaaggg cacgatatgg acttgtacat gtcgcaaaca ataattatga tccatggaat atatatgcta ttggtgggag ttcaaatcca accattctaa gtgaagggaa tagtttcact gccccaagtg agagctacaa gaaggaagta acaaagcgta tagggtgtga atcaccatca gcttgtgcga actgggtgtg gagatctaca cgagatgctt ttattaatgg agcttatttt gtatcatcgg ggaaaactga agagaccaat atatacaata gtaatgaagc tttcaaagtt gagaatggga atgcagctcc tcaattaacc aaaaatgctg gagttgtaac ctaa |
| Jun a 3 | AF121776 SEQ ID NO: 4 | atggcccgag tatcagagct tgcgtttctt cttgcggcca cattggccat ctctttacac atgcaagagg cgggagtagt gaagtttgat ataaagaacc agtgcggta cacagtctgg gcagcggggt tgcccggagg agggaagcgg cttgaccagg ggcagacatg gacggttaat ttggcggcgg gcacagcgtc ggcaaggttc tggggacgaa cgggctgcac tttcgatgcg agcgggaaag gaagctgcca gaccggtgac tgcggcgggc aactgagctg cacagtctcc ggagcagttc ccgcgacgct ggcagagtac acgcagagcg accaggacta ctacgacgta tccctcgtcg atggcttcaa cattcctctt gccatcaacc caacgaatgc acagtgcacc gctcctgcct gcaaggctga cattaatgca gtgtgcccttt ccgagttgaa ggttgatggc ggatgcaata gcgcctgcaa tgtcttcaaa actgatcagt attgctgcag aaatgcgtat gttgataact gccctgccac gaattactcc aagatattca agaaccagtg ccctcaggct tacagctatg ccaaggatga cacggccact ttcgcttgcg cctctggtac cgactacagt attgtattct gccctag |

TABLE 2

Amino acid sequences of Jun a 1 and Jun a 3 proteins and IgE epitopes

| | | Amino acid sequence | Residues |
|---|---|---|---|
| Jun a 1 Protein | | MASPCLIAVLVFLCAIVSCYSDNPID SCWRGDSNWDQNRMKLADCAVGFGSS TMGGKGGDFYTVTSTDDNPVNPTPGT LRYGATREKALWI<u>IFSQNMNIKLMP</u> LYVAGHKTIDGRGADVHLGNGGPCLF MRKVSHVILHSLHIHGCNTSVLGDVL VSESIGVEPVHAQDGDAITMRNVTNA WIDHNSLSDCSDGLIDVTLGSTGITI SNNHFFNHHKVMLLGHDDTYDDDKSM KVTV<u>AFNQFGPNAGQR</u> <u>MPRARYGLV</u> HVANNNYDPWNIYAIGGSSNPTILSE GNSFTAPSESYKKEVTKRIGCESPSA CANWV<u>WRSTRDAFINGAYFVSSGKTE</u> ETNIYNSNEAFKVENGNAAPQLTKNA GVVT (SEQ ID NO: 1) | |
| | Epitope | | |
| | 1 | IFSQNMNIKLKMP (SEQ ID NO: 5) | 71-83 |
| | 2 | AFNQFGPNAGQR (SEQ ID NO: 6) | 218-229 |
| | 3 | MPRARYGL (SEQ ID NO: 7) | 230-237 |
| | 4 | WRSTRDAFING (SEQ ID NO: 8) | 296-306 |
| Jun a 3 Protein | | MARVSELAFLLAATLAISLHMQEAGV VKFDIKNQCGYTVWAAGLPGGGKRLD QGQTWTVNL<u>AAGTASARFWGRTGC</u> <u>TFDASGLGSCQTG</u>DCGGQLSCTVSG AVPATLAEYTQSDQDYYDVSLVDGFN IPLAINPTNAQCTAPACK<u>ADINAVCP</u> <u>SELKVDGGCNSACNVFKT</u>DQYCCR<u>NA</u> <u>YVDNCPATNYSK</u>IFKNGCPQAYSYAK DDTATFACASGTDYSIVFCP (SEQ ID NO: 3) | 1-225 |
| | Epitope | | |
| | 1 | AAGTASARFWGRT (SEQ ID NO: 9) | 36-48 |
| | 2 | TFDASGKGSCQTG (SEQ ID NO: 10) | 51-63 |
| | 3 | ADINAVCPSELK (SEQ ID NO: 11) | 120-131 |
| | 4 | VDGGCNSACNVFKT (SEQ ID NO: 12) | 132-145 |
| | 5 | NAYVDNCPATNYSK (SEQ ID NO: 13) | 152-165 |

A goal of the present invention was to use a structurally characterized allergen and a unique monoclonal antibody (MAb) to that allergen to develop topically active or systemic agents, e.g., monoclonal antibody or a small molecule mimic, that could be administered into the nose or systemically to patients with cedar, cypress or juniper pollinosis during the pollination seasons. This agent(s) will act by a unique mechanism to prevent allergic symptoms.

In this regard, the present invention discloses the crystal structure of Jun a1 comprising locations of IgE epitopes (FIG. 1). Epitope 1 comprises amino acid residues 71-83, epitope 2 comprises amino acid residues 218-229, epitope 3 comprises amino acid residues 230-237 and epitope 4 comprises amino acid residues 296-306. The present invention discloses an anti-Jun a 1 monoclonal antibody E58 (mAb E58) that had an "anomalous" inhibition pattern in grouping assays. The grouping assays were based on the concept that two monoclonal antibodies that react with the same or spatially close regions of a protein, in this case Jun a 1 allergen from mountain cedar pollen, will inhibit the binding of each other to that protein. The anomalous result for monoclonal antibody E58 was that while none of the 21 monoclonal antibodies against Jun a 1 that were tested significantly inhibited the binding of E58 antibody, the E58 antibody inhibited >30% of the binding of 16 of these antibodies to Jun a 1 if E58 were added to Jun a 1 prior to the addition of the other antibodies (FIGS. 2A-2B). This result was particularly puzzling since all the 21 antibodies tested came from several different competition groups and thus, as a group recognized numerous spatially discrete sites on Jun a 1. It is contemplated that binding of monoclonal antibody E58 to Jun a 1 caused extensive structural changes, thereby reducing the ability of Jun a 1 to bind other mouse antibodies.

The present invention produced and characterized the E58 antibody, which extensively suppressed the binding of IgE from patients with cedar pollinosis (FIG. 3) and other mouse mAbs that recognize a multiple epitopes on Jun a1. The differences in the degree of E58's inhibitory activity on the pathogenic homologues of Jun a 1 (Cup s1 and Cry j1, FIG. 3) is probably due to differences in the affinity of E58's binding to each of the homologues.

The novelty of this finding is in the lack of similar effects of monoclonal antibodies on the binding of other antibodies to an allergen. For instance, while human IgG antibodies have "blocking" effects on the binding of IgE antibodies and activation of the allergic response cascade, these antibodies are polyclonal. Thus, their inhibitory effects may represent the sum of several different IgG antibodies, each binding to their unique site (epitope) and thereby preventing the binding of IgE to the same sites. There are also reports that a particular monoclonal antibody can inhibit a large part of IgE binding to an allergen (Bet v1 from birch pollen) (19). However, only two epitopes have been identified on Bet v1 allergen and they seem to be very close to each other. Thus, a single monoclonal antibody to Bet v1 might inhibit most or all of the human IgE binding, simply by steric hindrance, much as is seen with multiple members of a competing group of monoclonal antibodies. However, when a monoclonal antibody (Bip1) binds recombinant Bet v1, it induces structural modulation of Bet v1. This in turn enhances binding of human IgE from the sera of patients allergic to birch pollen to Bet v1 (20). In contrast, the instant invention discloses that the binding of E58 to Jun a1 allergen causes extensive structural alteration that inhibits the binding of IgE antibodies. Thus, the disclosure of the instant invention is novel. As a result, monoclonal antibody E58 is therapeutically effective whereas administration of an enhancing antibody would be predicted to worsen the allergic reactions to that allergen.

Further, the present invention created and evaluated engineered versions of mAb E58 with enhanced potency in down-modulating human IgE epitopes of Jun A1, Cup s 1 and Cry j 1. In this regard, a recombinant, single chain antibody (scAb) form of E58 (*E. coli* strain E-58 ScAb clone D6 comprising a plasmid encoding the E58 single chain antibody was deposited on May 1, 2013 with the Agricultural Research Culture Collections, International Depository Authority, 1815 N. University Street, Peoria, Ill., USA (NRRL) in compliance with the Budapest treaty on the international recognition of the deposit of microorganisms for the purpose of patent procedures and given NRRL deposit number B-50843)(FIG. 4) was produced, which can partially inhibit degranulation of IgE-sensitized mast cells was produced (FIG. 5).

The present invention further contemplates engineering this antibody to enhance both its avidity and ability to modulate multiple epitopes on Jun A1. Each version of the antibody is tested using immunochemical and biological assays for their ability to interrupt the relevant interaction between the cedar pollen allergens and the patient IgE antibodies. Selected versions of recombinant E58 antibody is tested in an animal model of cedar pollinosis.

The importance of the findings discussed herein is that one may use a monoclonal antibody such as monoclonal antibody E58 or a small molecule that mimics the effects of monoclonal antibody E58 binding to Jun a 1 to reduce the extent of allergic reactions to cedar pollens. Such mimics can be produced by defining the region of Jun a 1 that the monoclonal antibody E58 interacts with or more directly the regions of monoclonal antibody E58 that bind to Jun a 1. Ideally, this is done by co-crystallizing purified Jun a1 allergen-E58 antibody complexes. However, other experimental or computational approaches may be used in developing mimics of mAb E58's effects.

Some of the potential clinical applications of monoclonal antibody E58 or its mimics would be as follows. First, monoclonal antibody E58 or its mimics may be added to crude extracts of mountain or Japanese cedar pollen prior to using these extracts for immunotherapy for their respective diseases. This would reduce the local reactions at the injection sites caused by IgE antibodies in the sera of the individual, or even generalized reactions, and thereby allowing larger amounts of the extracts to be injected. This could reduce the number of injections required to induce the immunologic responses that ameliorate the allergic reactions.

Second, monoclonal antibody E58 or its mimics alone may be administered either topically in the nose or systemically into the circulation of an individual likely to develop allergic reactions to cedar pollens during pollination season for these trees. As a result of such administration, monoclonal antibody E58 or its mimics could then intercept the Group 1 allergens, e.g. Jun a 1 or Cry j 1, and reduce their ability to bind to individual's IgE antibodies. This would reduce the individual's reactions to these pollens.

Additionally, the results presented herein may also have broader implications to other types of immune response/reactions. For instance, most antibodies that "neutralize" the ability of microorganisms to infect their host are thought to bind to conformational epitopes on certain microbial antigens which are often called virulence factors for that organism. Thus, it is possible that these microorganisms persist in the immune individuals by producing other molecules that cause extensive changes in the structure of their surface proteins or toxins so that the host antibody response cannot bind and neutralize their infectivity or toxicity.

The present invention is directed to a monoclonal antibody or an antigen-binding fragment thereof directed against a Group I pollen allergen, where the monoclonal antibody or the antigen binding fragment thereof alters structure of the allergen thereby reducing or preventing the capacity of the allergen to interact with an IgE antibody. The Group I pollen allergen or the fragment thereof may have an amino acid sequence shown in SEQ ID NOS: 1, 3, 5, 6, 7, 8, 9, 10, 11, 12 or 13. Further, the Group I pollen allergen may be encoded by a nucleic acid sequence shown in SEQ ID NOS: 2 or 4. Examples of the Group I pollen allergen may include but is not limited to the ones isolated from cedar tree pollen, cypress tree pollen or juniper tree pollen. Additionally, the monoclonal antibody may be a murine, a chimeric, a humanized or a genetically engineered monoclonal antibody. Representative examples of the antibody may include but is not limited to E58 monoclonal antibody.

The present invention is also directed to an immunologic composition, comprising the above-described monoclonal antibody or the antigen binding fragment thereof and a pharmaceutically acceptable carrier.

The present invention is further directed to a method of preventing development of an allergic reaction to a pollen in an individual, comprising the step of: administering therapeutically effective amounts of the immunologic composition described supra to the individual. The administered immunologic composition may alter ability of one or more than one pollen allergen or a fragment thereof to bind to an IgE antibody of the individual. The allergen or the fragment thereof may have an amino acid sequence shown in SEQ ID NOS: 1, 3, 5, 6, 7, 8, 9, 10, 11, 12 or 13. Further, the allergen may be encoded by a nucleic acid sequence with SEQ ID NOS: 2 or 4. Additionally, the pollen may include but is not limited to the ones from cedar tree, cypress tree or juniper tree. Furthermore, the individual benefiting from such a method may be an individual likely to suffer from allergic reactions when exposed to the pollen. Examples of the allergic reaction may include but is not limited to allergic rhinitis, atopic dermatitis, asthma or utricaria. Additionally, the immunologic composition may be administered topically in nose of the individual, by inhalation into the lungs or systemically into circulation of the individual.

The present invention is also directed to an immunologic composition, comprising the monoclonal antibody or the antigen-binding fragment thereof described supra, crude extract of pollen and a pharmaceutically acceptable carrier. The crude extract of the pollen in such a composition may comprise an allergen or a fragment thereof with an amino acid sequence shown in SEQ ID NO: 1, 3, 5, 6, 7, 8, 9, 10, 11, 12 or 13. Further, the allergen or the fragment thereof may be encoded by a nucleic acid sequence with SEQ ID NOS: 2 or 4. Examples of the pollen may include but is not limited to ones from cedar tree, cypress tree or juniper tree.

The present invention is further directed to a method of improving pollen allergy immunotherapy in an individual, comprising the step of administering therapeutically effective amounts of the immunologic composition described supra to the individual. This administration may reduce local reactions at the injection sites, thereby allowing larger amounts of the extracts to be injected and reducing the number of injections required to induce the immunologic responses that ameliorate allergic reactions. Additionally, the individual benefiting from such a method may be one who is an individual likely to suffer from allergic reactions when exposed to pollen. Examples of the allergic reaction may include but are not limited to allergic rhinitis, atopic dermatitis, asthma or utricaria. Additionally, the immunologic composition may be administered subcutaneously to the individual.

The present invention is still further directed to a monoclonal antibody or an antigen binding fragment thereof directed against a homologue or a fragment thereof that is at least 90% identical to the amino acid sequence of the Group I pollen allergen or a fragment thereof, where the monoclonal antibody or the antigen binding fragment thereof alters structure of the homologue or the fragment thereof, inhibits binding of IgE antibody to the homologue or the fragment thereof or both. Such a homologue or the fragment thereof may be at least 90% identical to the amino acid sequence shown in SEQ ID NOS: 1, 3, 5, 6, 7, 8, 9, 10, 11, 12 or 13. Further, the homologue or the fragment thereof may be at least 90% identical to the amino acid sequence encoded by a nucleic acid sequence of SEQ ID NOS: 2 or 4. The Group I pollen allergen or the fragment thereof may be one that is isolated from cedar tree pollen, cypress tree pollen or juniper tree pollen. Furthermore, monoclonal antibody is a murine, a chimeric, a humanized or a genetically engineered monoclonal antibody.

The present invention is also directed to an immunologic composition, comprising the monoclonal antibody or the antigen binding fragment thereof described supra and a pharmaceutically acceptable carrier.

The present invention is still further directed to a method of preventing development of an allergic reaction to a pollen in an individual, comprising the step of: administering therapeutically effective amounts of the immunologic composition described supra to the individual. In such a method, the administered immunologic composition may alter ability of one or more than one of the homologue or the fragment thereof to bind to the IgE antibody of the individual. Examples of the pollen may include but is not limited to the one from cedar tree, cypress tree or juniper tree. Further, the individual benefiting from such a method may include but is not limited to one who is an individual likely to suffer from allergic reactions when exposed to pollen. Furthermore, examples of the allergic reaction may include but is not limited to allergic rhinitis, atopic dermatitis, asthma or utricaria. Additionally, the immunologic composition may be administered topically in nose of the individual or systemically into circulation of the individual.

The present invention is still further directed to an immunologic composition, comprising the monoclonal antibody or the antigen binding fragment thereof described supra, crude extracts of Group I pollens and a pharmaceutically acceptable carrier. The crude extracts of Group 1 pollens in such a composition may comprise an allergen with an amino acid sequence shown in SEQ ID NO: 1, 3, 5, 6, 7, 8, 9, 10, 11, 12 or 13 or a fragment thereof. Additionally, the allergen may be encoded by a nucleic acid sequence shown in SEQ ID NOS: 2 or 4. Example of the Group I pollen may include but is not limited to the ones from cedar tree, cypress tree or juniper tree.

The present invention is also directed to a method of improving pollen allergy immunotherapy in an individual, comprising the step of administering therapeutically effective amounts of the above-described immunologic composition to the individual. This administration may reduce local reactions at the injection sites, thereby allowing larger amounts of the extracts to be injected and reducing the number of injections required to induce the immunologic responses that ameliorate allergic reactions. Individuals benefiting from such a method may include but is not limited to an individual likely to suffer from allergic reactions when exposed to Group 1 pollen allergens. Examples of the allergic reaction may include but is not limited to allergic rhinitis, atopic dermatitis, asthma or utricaria. The immunologic composition in such a method may be administered subcutaneously to the individual.

The present invention is further directed to a monoclonal antibody or an antigen binding fragment thereof directed against a homologue or a fragment thereof that is at least 80% identical to the amino acid sequence of the Group I pollen allergen or a fragment thereof, where the monoclonal antibody or the antigen binding fragment thereof alters structure of the homologue or the fragment thereof, inhibits the binding of an IgE antibody to the homologue or the fragment thereof or both. All other aspects regarding the amino acid sequence that the homologue or the fragment thereof is identical to, the nucleic acid sequence encoding the amino acid sequences, examples of the source of the Group 1 pollen allergen, type of monoclonal antibody and specific examples of the monoclonal antibody is the same as discussed supra.

The present invention is still further directed to an immunologic composition, comprising the monoclonal antibody or the antigen binding fragment thereof described supra and a pharmaceutically acceptable carrier.

The present invention is also directed to a method of preventing development of an allergic reaction to pollen in an individual, comprising the step of: administering therapeutically effective amounts of the immunologic composition described supra to the individual. All other aspects regarding the effect of the homologue or the fragment thereof, examples of the source of the pollen, the type of individual benefiting from such a method, examples of the allergic reaction and route of administration of the immunologic composition is the same as described supra.

The present invention is further directed to an immunologic composition, comprising the monoclonal antibody or the antigen binding fragment thereof described supra, crude extracts of Group I pollens and a pharmaceutically acceptable carrier. All other aspects regarding the amino acid and nucleic acid sequences of the allergen in the crude extract and the source of Group I pollen is the same as described supra.

The present invention is also directed to a method of providing immunoprotection against Group I pollens in an individual, comprising the step of administering therapeutically effective amounts of the immunologic composition described supra to the individual. All other aspects regarding the effect of such an administration, the types of individual benefiting from such a method, examples of allergic reaction, and route of administration is the same as discussed supra.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. Some embodiments of the invention may consist of or consist essentially of one or more elements, method steps, and/or methods of the invention. It is contemplated that any method or composition described herein can be implemented with respect to any other method or composition described herein.

As used herein, the term "therapeutically effective amount" refers to an amount that results in an improvement or remediation of the symptoms of the disease or condition due to induction of an immune response. Those of skill in the art understand that the effective amount may improve the patient's or subject's condition, but may not be a complete cure of the disease and/or condition.

As used herein, a sequence that is at least 90% homologous to amino acid sequence of Group I pollen allergen may comprise a sequence that is 99%, 98%, 97%, 96%, 95%, 94%, 93%, 92%, 91% or 90% homologous to Group I pollen allergen. Similarly, as used herein, a sequence that is at least 80% homologous to amino acid sequence of Group I pollen allergen may comprise a sequence that is 99%, 98%, 97%, 96%, 95%, 94%, 93%, 92%, 91%, 90%, 89%, 88%, 87%, 86%, 85%, 84%, 83%, 82%, 81% or 80% homologous to Group I pollen allergen.

The therapeutically effective amount of the immunologic composition to be used are those amounts effective to produce beneficial results, particularly with respect to reducing the allergenic response by inducing T cell helper response. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated.

Preferred animal models for use in certain embodiments are rodent models, which are preferred because they are economical to use and, particularly, because the results gained are widely accepted as predictive of clinical value.

As used herein, the monoclonal antibody of the present invention may be generated by any of the methods that are known in the art. These antibodies may be murine, chimeric, humanized, human or genetically engineered using mammalian cell, bacterial cell, plant cell or yeast cell. Additionally, the fragment of such an antibody may comprise a monovalent antigen binding fragment (Fab) that consists of one light chain and part of one heavy chain, a bivalent antigen binding fragment (F(ab)$_2$) that consists of both light chains and part of both heavy chains, a single chain variable fragment or a single chain antibody.

The immunologic composition disclosed herein may be administered either alone or in combination with another drug, a compound, or an antibiotic. Such a drug, compound or antibiotic may be administered concurrently or sequentially with the immunologic composition. The effect of co-administration with the immunologic composition is to lower the dosage of the drug, the compound or the antibiotic normally required that is known to have at least a minimal pharmacological or therapeutic effect against the disease that is being treated. Concomitantly, toxicity of the drug, the compound or the antibiotic to normal cells, tissues and organs is reduced without reducing, ameliorating, eliminating or otherwise interfering with any cytotoxic, cytostatic, apoptotic or other killing or inhibitory therapeutic effect of the drug, compound or antibiotic.

The composition described herein and the drug, compound, or antibiotic may be administered independently, either systemically or locally, by any method standard in the art, for example, subcutaneously, parenterally, intraperitoneally, intradermally, intramuscularly, topically, nasally, or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The immunologic composition described herein may be administered independently one or more times to achieve, maintain or improve upon a therapeutic effect. It is well within the skill of an artisan to determine dosage or whether a suitable dosage of either or both of the immunologic composition or antibody comprises a single administered dose or multiple administered doses.

As is well known in the art, a specific dose level of such an immunologic composition for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Identification and Characterization of Anti-Allergen Monoclonal Antibody

Previous studies had identified two major allergens. One of them, Jun a 1 has an amino acid and nucleic acid sequence shown in SEQ ID NOS: 1 and 2, respectively (21). The other, Jun a 3 has an amino acid and nucleic acid a nucleic acid and an amino acid sequence shown in SEQ ID NOS: 3 and 4, respectively.

Screening of a large panel of anti-Jun a 1 monoclonal antibodies by grouping assay led to an anomalous inhibition pattern exhibited by one of the monoclonal antibodies. Briefly, the grouping assays are based on the concept that two monoclonal antibodies that react with the same or spatially close regions of a protein will inhibit the binding of each other to that protein. While none of the 21 antibodies inhibited the binding of E58 monoclonal antibody to Jun a 1, E58 monoclonal antibody when added to Jun a 1 first inhibited>30% of the binding of the 16 of these antibodies to Jun a 1 (FIGS. 2A-2B).

Further, whether E58 antibody prevented the binding of IgE antibodies from patients who are allergic to mountain cedar pollen and thereby reduce the potential of Jun a 1 to cause allergic reaction was determined. Allergen coated wells were preincubate with 10 μg/ml mAb E58 prior to adding patient sera. Human IgE was detected by biotinylated anti-human IgE followed by HRP-avidin (FIG. 3). Prior binding of E58 antibody inhibited the binding of 50-60% of the serum IgE antibodies from 11 patients with mountain cedar sensitivity. While several other mouse monoclonal antibodies to Jun a1 inhibited some human IgE antibody binding, it was always in the range of 20-30% inhibition.

Similarly, the binding of IgE antibodies from patients with Japanese cedar sensitivity were inhibited from binding to Cry j 1, a structurally homologous allergen from Japanese cedar pollen. The extent of this inhibition was less than that for Jun a 1-anti-Jun a 1 complexes. This was most likely due to lower avidity of the E58 binding to Cry j 1. This is indicated by the relatively smaller effect of E58 binding on the binding of E58 to Cry j1. This can be overcome by increasing the concentration of labeled E58 monoclonal antibody. Thus, the E58 antibody inhibited the binding of IgE antibodies to Jun a 1 and to a lesser extent of IgE anti-Cry j 1 antibodies to this Jun a 1 homologue. Additionally, a recombinant, single chain antibody (scAb) form of E58 (FIG. 4) was produced. It was observed that this scAb form of E58 partially inhibited degranulation of IgE-sensitized mast cells (FIG. 5).

Example 2

Production of Engineered, High Affinity Versions of E58 and their Ability in Suppressing Jun a 1's Ability to Bind Human IgE Antibodies The present invention contemplates using APEx (Antibody enhancement technology) to produce high affinity versions of E58. Briefly, the APEx method involves 1) anchoring an antibody of interest, usually in the form of a single chain containing both variable region fragments (scFv), to the outer surface of the *E. coli* inner membrane, 2) removal of the outer membrane with lysozyme/detergent to produce spheroplasts which are covered with the now-exposed antibodies, 3) incubation of the antibody-displaying spheroplasts with limiting amounts of fluorescently labeled antigen, and 4) isolation of spheroplasts displaying active Abs using fluorescence activated cell sorting (FACS). Anchoring to the outer surface of the inner membrane is achieved by fusing the antibody fragment to an NlpA anchoring sequence that is fatty acylated in vivo. This approach has proven far more effective than anchoring to the outer membrane, due to steric interference from outer membrane components. Multiple rounds of antibody sequence diversification/FACS sorting are used to evolve enhanced antibody affinity and desired specificity or function.

The gene for the E58 antibody has been cloned from the parent E58 hybridoma, and expressed in active, scAb form in *E. coli*. The misfolding issues are the only barrier to successful Ab enhancement using APEx. Therefore, the stage is entirely set for affinity and functional enhancement of E58, using APEx.

Since FACS machines can sort based on monitoring multiple fluorescent wavelengths simultaneously, a distinct advantage of the FACS-based approach is that several characteristics of an antibody can be selected in a single, high throughput sorting experiment. This capability is utilized by incubating the Ab-displaying spheroplasts with limiting quantity of tetramethyl rhodamine (TMR)-labeled Jun a 1. After washing, the bacteria are incubated with patient sera, followed by FITC-labeled mAb to human IgE. In the FACS, events with high TMR staining, but relatively low FITC signal are selected. Thus, these clones are capable of tightly binding Jun a 1 in a way that extensively down-modulates its capacity to bind human IgE. If initial results indicate that whole human serum causes background fluorescence, the IgE will be purified by mAb affinity chromatography or one may substitute mouse mAbs that mimic human IgE Abs.

The APEx technology allows expression of E58 variants in both single chain and whole IgG (22) format so the role of mono vs. mutivalence and the presence of Fc regions are assessed. Further, because antibody fragments are produced economically and in large quantities in bacteria, a source of engineered antibody fragments is readily available for the animal studies.

Example 3

Inhibition of Activation of Cultured Mast Cells and Blood Basophils Sensitized with Human IgE Antibodies and Exposed to Purified Jun a1 Allergen Mast cells and basophils are the major cell types that mediate the allergic reactions after cross-linking of their FcER1 by IgE Ab-allergen complexes. Based on the activity of E58 in ELISA assays (FIG. 3), the binding of specifically engineered E58 to Jun a 1 should substantially reduce Jun a 1's ability to cross-link patient IgE attached to the FcER1 on the surface of mast cells and basophils, thereby preventing the Jun a 1-induced release of allergic mediators. Increased affinity and perhaps subtle changes in the epitope recognized on Jun a 1 should enhance the effectiveness of the engineered, relative to native E58.

This concept is tested using cultured mast cells transfected with a plasmid expressing human FcER1 alpha chain (23; RBL-SX 38, Dr. J. P. Kinet, Harvard Medical School). These cells are incubated overnight with sera of patients with cedar pollinosis to "arm" them with IgE Abs and then stimulated with purified Jun a 1 alone or Jun a 1 that has been preincubated with varying concentrations of engineered E58 for 30 min at 37° C. The release of β-hexosaminidase, a marker of degranulation/mediator release, into the supernatant after 30 min is quantified as described (24-25) and the percent of inhibition of Jun a 1-induced release by E58 calculated. Controls for these experiments include RBL-SX38 cells stimulated with the $Ca^{2+}$ ionophore ($10^{-5}$ M) and serum-sensitized cells that are cross-linked with anti-IgE Abs (Sigma, St. Louis, Mo.). FIG. 5 in the present invention shows the effect of 2 and 20 µg/ml of the scAb derived from mouse E58 mAb variable region sequences. These results indicate that while the original antibody partially inhibits the Jun a 1-induced degranulation of sensitized RBL-SX38 cells, it requires high concentration of the scAb, suggesting that antibody engineering is required to optimize E58's inhibitory activity. The results of these RBL experiments are confirmed using peripheral blood basophils armed with the IgE from the same patient sera (26).

Example 4

Development and Testing of a System for Effective Delivery of Engineered E58 to the Nasal Mucosa in a Mouse Model of Cedar Pollinosis Recombinant, engineered E58 could be effective when administered either topically in the nose or systemically. However, instillation directly into the nasal cavity would have a number of advantages. Topical Abs will provide a higher local concentration at the site of pollen exposure than systemic injection of Ab, thereby reducing their cost and the potential for adverse reactions. However, topical administration may require special formulation to keep the agent from being rapidly cleared by the mucocilliary apparatus in the nose.

A primary goal of the experiments proposed here is to demonstrate that engineered E58 Abs, when given nasally can inhibit or reduce the allergic inflammation induced by a juxtaposed nasal challenge with cedar pollen or purified Jun a 1. A mouse model of allergic rhinitis has been described and validated (27-28) in which Balb/c mice are immunized in a classical manner for allergic asthma, i.e., intraperitoneal priming with allergen in alum, followed by multiple topical exposures to the same allergen in saline. To assess the intranasal response, allergen is instilled in the nose of the unanesthesized mice and the degree of nasal obstruction is monitored using whole body plethysmography in the Buxco unit or the Flexivent system (28). A protective role for the engineered E58 Ab in mice sensitized with Jun a 1 is assessed by administering varying concentrations of the antibody into the nasal cavity, at various intervals prior to the instillation of purified Jun a 1 or cedar pollen. The change in respiratory parameters after allergen challenge is calculated relative to the respiratory rate after saline challenge or by upper airway resistance, as measured by Flexivent. Samples of nasal tissue are collected after allergen challenge and hematoxilin/eosin stained sections are analyzed for the degree of eosinophil infiltration.

Example 5

Preincubation of Jun a 1 with scAb Derived from E58 Inhibits the Jun a 1-Induced Release of 6-Hexosaminidase from RBL-SX38

Cells were sensitized by incubating overnight with 1:10 dilution of patient sera. Sensitized cells were incubated with 0-20 µg/ml scAb and 10 ng/ml Jun a 1 for 4 hrs, and the release of the granular marker β-hexosaminidase was measured in the culture supernatant (FIG. 6). The results indicate that mast cell mediator release was inhibited for all three sera tested although the degree of the inhibition may be limited by the affinity of these monovalent, recombinant antibodies.

Example 6

Animal Model for Allergic Rhinitis

Female Balb/c mice 8 weeks of age were immunized by intraperitoneal injections of 10 µg of ovalbumin (OVA) with aluminum hydroxide (alum), followed by daily nasal instillation of OVA in PBS from days 28 to 33. Immediately after the last intranasal dose the mice were place in a whole body plethysmograph and expiratory frequency (Rf) was analyzed as a measure of the increased nasal resistance caused by the early phase (up to 60 min) nasal allergic responses (FIG. 7).

The following references were cited herein:
1. Midoro-Horiuti et al. (1992), *Acta Paediatr Jpn* 34: 501-504.
2. Platts-Mills et al. (1998) *J Allergy Clin Immunol* 102: 335-343.
3. Malone et at (1997) *J Allergy Clin Immunol* 99: 22-27.
4. Fireman (1997) *Allergy & Asthma Proceedings* 18: 63-67.
5. Sato et al (1997) *Ann Allergy Asthma Immunol* 79: 57-61.
6. Goetz et at (1995) *Ann Allergy Asthma Immunol* 75: 256-260.
7. Schwietz et al (2000) *Ann Allergy Asthma Immunol* 84: 87-93.
8. Panzani et al (1986) *Ann Allergy* 56: 460-463.
9. Ford (1991) *International Arch Allergy Appl Immunol* 95: 178-183.
10. Rogers and Croft (1999) *J Immunol* 163: 1205-1213.
11. Kay (2001) *N Engl J Med* 344: 109-113.
12. Durham and Till (1998) *J Allergy Clin Immuno* 102: 157-164.
13. Akidis et al (1996) *J Clin Invest* 98: 1676-1683.
14. Durham et al (1999) *N Engl J Med* 341: 468-475.
15. Ferreira et at (1996) *J Exp Med* 183: 599-609.
16. Ferreira et al (1997) *Int Arch Allergy Immunol* 113: 125-127.
17. Midoro-Horiuti et al. (1999), *J Allergy Clin Immunol* 104: 608-612.
18. Czerwinski et al. (2005), *J Biol Chem* 280: 3740-3746.
19. Spangfort et al (2003) *J Immunol* 171: 3084-3090.
20. Laffer et al (1996) *J Immunology* 157: 4953-4962.
21. Midoro-Horiuti et al. (1999), *J Allergy Clin Immunol* 104: 613-617.
22. Mazor et al (2007) *Nat Biotechnol* 25(5): 563.
23. Wiegand et al (1996) *J Immunol* 157(1): 221.
24. Zaitsu et al (2007) *Mol Immunol* 44(8): 1987.
25. Narita et al (2007) *Env Health Perspectives* 115(1): 48.
26. Purohit et al (2005) *Clin Exp Allergy* 35(2): 186.
27. Miyahara et al. (2005) *J Allergy Clin Immunol* 116(5): 1020.
28. Miyahara et al (2006) *J Allergy Clin Immunol* 118(5): 1110.

Any patents or publications mentioned in this specification are indicative of the levels of those skilled in the art to which the invention pertains. Further, these patents and publications are incorporated by reference herein to the same extent as if each individual publication was specifically and individually incorporated by reference.

What is claimed is:

1. An E58 antibody, encoded by deposit B-50843 (*E. coli* strain E-58 ScAb clone D6) deposited with the Agricultural Research Culture Collections, or an antigen-binding fragment thereof that binds a protein having the amino acid sequence of SEQ ID NO:1, wherein said E58 antibody or the antigen binding fragment thereof reduces or prevents the protein having the amino acid sequence of SEQ ID NO:1 from interacting with IgE.

2. A therapeutic composition, comprising: the E58 antibody or the antigen binding fragment thereof of claim 1, crude extract of pollen comprising an allergen comprising an amino acid sequence of SEQ ID NO: 1, and a pharmaceutically acceptable carrier.

3. A composition, comprising:
the E58 antibody or the antigen binding fragment thereof of claim 1, crude extracts of Group I pollens and a pharmaceutically acceptable carrier.

4. An E58 antibody, encoded by deposit B-50843 (*E. coli* strain E-58 ScAb clone D6) deposited with the Agricultural Research Culture Collections, that binds a pollen allergen having the amino acid sequence of SEQ ID NO:1, wherein said E58 antibody reduces or prevents the allergen from interacting with another antibody at more than one epitope.

5. A method of treating allergies in an individual, comprising the step of: administering a E58 antibody or antigen binding fragment of claim 1 to the individual.

6. The method of claim 5, wherein the E58 antibody or antigen binding fragment thereof is administered topically in the nose of the individual or systemically into circulation of the individual.

* * * * *